United States Patent [19]

Hoeschele et al.

[11] Patent Number: 4,868,062

[45] Date of Patent: Sep. 19, 1989

[54] VAPOR PERMEABLE POLY(ETHERIMIDE) ESTER ELASTOMER FILMS

[75] Inventors: Guenther K. Hoeschele; George J. Ostapchenko, both of Wilmington, Del.

[73] Assignee: E. I. Du Pont de Nemours and Company, Wilmington, Del.

[21] Appl. No.: 137,975

[22] Filed: Dec. 28, 1987

[51] Int. Cl.$^4$ .................... B32B 27/00; C08G 69/44; C08G 73/10
[52] U.S. Cl. ................. 428/423.1; 428/473.5; 428/480; 528/289; 528/322
[58] Field of Search .................. 528/289, 322; 428/423.1, 473.5, 480

[56] References Cited

U.S. PATENT DOCUMENTS

| | | | |
|---|---|---|---|
| 4,493,870 | 1/1985 | Vrouenraets et al. | 428/245 |
| 4,556,688 | 12/1985 | McCready et al. | 525/33 |
| 4,556,705 | 12/1985 | McCready | 528/289 |
| 4,636,442 | 1/1987 | Beavers et al. | 428/480 |
| 4,714,754 | 12/1987 | McCready et al. | 528/296 |
| 4,725,481 | 2/1988 | Ostapchenko | 428/213 |

*Primary Examiner*—Harold D. Anderson
*Assistant Examiner*—Dennis R. Daley

[57] ABSTRACT

A flexible breathable waterproof product of a film of a thermoplastic hydrophilic poly(etherimide) ester elastomer which is the reaction product of one or more diols, one or more dicarboxylic acids, and one or more poly(oxyalkylene imide) diacids said poly(oxyalkylene imide) diacid containing sufficient repeating units of ethylene oxide so that the resulting poly(etherimide) ester elastomer has about 25–60 weight percent ethylene oxide units and said film has a water vapor transmission rate of at least about 3500 gm mil/m$^2$/24 hours according to ASTM E96-66 (Procedure BW).

9 Claims, No Drawings

VAPOR PERMEABLE POLY(ETHERIMIDE) ESTER ELASTOMER FILMS

BACKGROUND OF THE INVENTION

The present invention is directed to a vapor permeable, waterproof film for use as surgical drape and in waterproof apparel and equipment.

The textile industry has manufactured breathable fabrics composed of a film of a polymeric material that is permeable to water vapor bonded to a textile material. The most notable and successful material that transmits water vapor therethrough is a film of microporous polytetrafluoroethylene that is adhered to a textile material. Although this product has been commercially successful, it is rather expensive and the pores tend to be blocked by dirt, body oils and detergents. There is a need for a waterproof film having good physical properties, good wear resistant characteristics, and lower cost.

SUMMARY OF THE INVENTION

The present invention is directed to a flexible, breathable, waterproof product which comprises a film of a thermoplastic hydrophilic poly(etherimide) ester elastomer comprising the reaction product of one or more diols, one or more dicarboxylic acids, and one or more poly(oxyalkylene imide) diacids said poly(oxyalkylene imide) diacid containing sufficient repeating units of ethylene oxide so that the resulting poly(etherimide) ester elastomer contains about 25–60 weight percent ethylene oxide units and said film has a water vapor transmission rate of at least 3500 gm.mil/m$^2$/24 hrs. according to ASTM E96-66 (Procedure BW).

The hydrophilic poly(etherimide) ester elastomer film can be attached to a textile material, either woven or nonwoven, to form a flexible layered product for use in breathable water-resistant articles and apparel.

By content of repeating units of ethylene oxide in the poly(etherimide) ester elastomer is meant the weight percent in the elastomer of repeating units of ($CH_2$—$CH_2$—O—) derived from the poly(oxyalkylene imide) diacid.

The breathable water resistant film is useful as surgical drape or can be attached to textile materials for use in making breathable, water vapor permeable articles, such as raincoats, tents and gloves.

DESCRIPTION OF PREFERRED EMBODIMENTS

The poly(etherimide) ester elastomers used in the present invention are prepared by conventional processes from (a) one or more diols, (b) one or more dicarboxylic acids and (c) one or more poly(oxyalkylene imide) diacids. Preferred poly(etherimide) esters can be prepared when the diol (a) is one or more $C_2$-$C_{15}$ aliphatic and/or cycloaliphatic diols, when the dicarboxylic acid (b) is one or more $C_4$-$C_{16}$ aliphatic, cycloaliphatic and/or aromatic dicarboxylic acids or ester derivatives thereof and when the poly(oxyalkylene imide) diacid (c)is derived from one·or more polyoxyalkylene diamines and one or more tricarboxylic acid compounds containing two vicinal carboxyl groups or an anhydride group and an additional carboxyl group. The poly(oxyalkylene imide) diacids must contain sufficient repeating units of ethylene oxide so that the resulting poly(etherimide) ester elastomer contains from about 25 to 60 weight percent ethylene oxide units. In general, the weight ratio of poly(oxyalkylene imide) diacid (c) to dicarboxylic acid (b) is from about 0.5 to 4, preferably from about 0.8 to about 3.

Suitable diols (a) for use in preparing the poly(etherimide) ester elastomers include saturated and unsaturated aliphatic and cycloaliphatic dihydroxy compounds as well as aromatic dihydroxy compounds. These diols, preferably, have low molecular weights, i.e. having a molecular weight of about 250 or less. When used herein, the term "diols" and "low molecular weight diols" should be construed to include equivalent ester forming derivatives thereof, provided, however, that the molecular weight requirement pertains to the diol only and not to its derivatives. Exemplary ester forming derivatives are acetates of the diols as well as, for example, ethylene oxide or ethylene carbonate for ethylene glycol.

Preferred saturated and unsaturated aliphatic and cycloaliphatic diols are those having from about 2 to 15 carbon atoms. Representative diols include ethylene glycol; 1,3-propanediol; 1,4-butanediol; 1,5-pentanediol; 2-methylpropanediol; 2,2-dimethyl propanediol; 1.6-hexanediol; 1,10-decanediol; 1,2-1,3- and 1,4-dihydroxy cyclohexane; 1,2-, 1,3- and 1,4-cyclohexane dimethanol; 1,4-butenediol mixed with major amounts of 1,4-butanediol. 1,4-butanediol is especially preferred.

Aromatic diols used are generally those having from 6 to 15 carbon atoms. Included among the aromatic dihydroxy compounds are resorcinol; hydroquinone; 1,5-dihydroxynapthalene; 4,4,-dihydroxydiphenyl; bis(p-hydroxyphenyl)methane and bis(p-hydroxyphenyl)propane.

Especially preferred diols are the saturated aliphatic diols, mixtures thereof and mixtures of a saturated diol(s) with an unsaturated diol(s), wherein each diol contains from 2 to about 8 carbon atoms. Where more than one diol is employed, it is preferred that at least about 60 mole %, based on the total diol content, be the same diol, most preferably at least 80 mole %. As mentioned above, the preferred compositions are those in which 1,4-butanediol is present in a predominant amount, most preferably when 1,4-butanediol is the only diol used.

Dicarboxylic acids (b) which are used to make the poly(etherimide) ester elastomers are aliphatic, cycloaliphatic, and/or aromatic dicarboxylic acids. Preferably, these acids have low molecular weights, i.e., having a molecular weight of less than about 300; however, higher molecular weight dicarboxylic acids, especially dimer acids, may be used. The term "dicarboxylic acids" as used herein, includes equivalents of dicarboxylic acids having two functional groups which perform substantially like dicarboxylic acids in reaction with glycols and diols in forming polyester polymers. These equivalents include esters and ester-forming derivatives, such as acid halides and anhydrides. The molecular weight preference, mentioned above, pertains to the acid and not to its equivalent ester or ester-forming derivative. Thus, an ester of a dicarboxylic acid having a molecular weight greater than 300 or an acid equivalent of a dicarboxylic acid having a molecular weight greater than 300 are included provided the acid has a molecular weight below about 300.

Aliphatic dicarboxylic acids, as the term isused herein, refers to carboxylic acids having two carboxyl groups each of which is attached to a saturated carbon atom. If the carbon atom to which the carboxyl group is attached is in a ring, the acid is cycloaliphatic.

Representative aliphatic and cycloaliphatic acids which can be used are sebacic acid, 1,2-cyclohexanedicarboxylic acid, 1,3-cyclohexanedicarboxylic acid, 1,4-cyclohexanedicarboxylic acid, adipic acid, glutaric acid, succinic acid, oxalic acid, azelaic acid, diethylmalonic acid, allylmalonic acid, dimer acid, 4-cyclohexene-1,2-dicarboxylic acid, 2-ethylsuberic acid, cyclopentanedicarboxylic acid, decahydro-1,5-naphthalenedicarboxylic acid, 4,4,-bicyclohexyldicarboxylic acid, decahydro-2,6-naphthalenedicarboxylic acid, 4,4-methylenebis(cyclohexanecarboxylic acid), 3,4-furandicarboxylic acid. Preferred aliphatic acids are cyclohexane dicarboxylic acids, sebacic acid, glutaric acid, azelaic acid and adipic acid.

Aromatic dicarboxylic acids, as the term is used herein, are dicarboxylic acids having two carboxyl groups each of which is attached to a carbon atom in an isolated or fused benzene ring system. It is not necessary that both functional carboxyl groups be attached to the same aromatic ring, and where more than one ring is present, they can be joined by aliphatic or aromatic divalent radicals such as —O— or —SO$_2$—.

Representative aromatic dicarboxylic acids which can be used include terephthalic, phthalic and isophthalic acids, bi-benzoic acid, substituted dicarboxy compounds with two benzene nuclei such as bis(p-carboxyphenyl)methane, oxybis(benzoic acid), ethylene-1,2-bis-(p-oxybenzoic acid), 1,5-naphthalenedicarboxylic acid, 2,6-naphthalenedicarboxylic acid, 2,7-naphthalenedicarboxylic acid, phenanthrenedicarboxylic acid, anthracenedicarboxylic acid, 4,4,-sulfonyldibenzoic acid, and halo and $C_1$-$C_{12}$ alkyl, alkoxy, and aryl ring substitution derivatives thereof. Hydroxy acids such as p($\beta$-hydroxyethoxy) benzoic acid can also be used provided an aromatic dicarboxylic acid is also present.

Preferred dicarboxylic acids for the preparation of the poly(etherimide) ester elastomers are the aromatic dicarboxylic acids, mixtures thereof and mixtures of one or more dicarboxylic acids with an aliphatic and/or cycloaliphatic dicarboxylic acid, and most preferably, only aromatic dicarboxylic acids are used. Aromatic dicarboxylic acids with 8–16 carbon atoms are preferred, most preferably the benzenedicarboxylic acids, i.e., phthalic, terephthalic and isophthalic acids and their dimethyl derivatives. Especially preferred is dimethyl terephthalate.

Finally, where mixtures of dicarboxylic acids are employed, it is preferred that at least about 60 mole %, preferably at least about 80 mole %, based on 100 mole % of dicarboxylic acid (b) be the same dicarboxylic acid or ester derivative thereof. As mentioned above, the preferred compositions are those in which dimethyl terephthalate is the predominant dicarboxylic acid, most preferably when dimethyl terephthalate is the only dicarboxylic acid.

Poly(oxyalkylene imide) diacids (c) suitable for use herein are high molecular weight imide diacids wherein the average molecular weight is greater than about 900, most preferably greater than about 12000. They may be prepared by the imidization reaction of one or more tricarboxylic acid compounds containing two vicinal carboxyl groups or an anhydride group and an additional carboxyl group which must be esterifiable and, preferably, is nonimidizable with a high molecular weight poly(oxylalkylene) diamine. The high molecular weight polyoxyalkylene diamines used to prepare the poly(oxyalkylene imide) diacids generally have the formula H$_2$N—G—NH$_2$ where G is a divalent radical remaining after removal of hydroxyl groups of a long chain ether glycol having a molecular weight of from about 600–6000, usually 900–4000. The polyalkylene diamines are those usually having 2–5 carbon atoms in the alkylene group. Representative polyoxyalkylene diamines include polyoxyethylene diamine, polyoxypropylene diamine, polyoxybutylene diamine and the like.

A special class of poly(oxyalkylene imide) diacids is prepared by imidization of a high molecuar weight poly(oxyalkylene) diamine with one or more tricarboxylic acid compounds containing two vicinal carboxyl groups or an anhydride group and an additional carboxyl group in the presence of pyromellitic anhydride. The number of equivalents of anhydride or vicinal carboxylic acid functions provided by the tricarboxylic acid compounds and pyromellitic anhydride should be the same as the total number of amine functions. Generally, the molar ratio of pyromellitic anhydride to the tricarboxylic acid compounds containing two vicinal carboxylic acid groups or an anhydride group and an acid group ranges from 0.33 to 1.5. This modification with pyromellitic anhydride increases the molecular weight of the poly(oxyalkylene imide) diacids and increases the hydrophilic nature of the resulting poly(etherimide) ester elastomer.

In general, preferred poly(oxyalkylene imide) diacids useful herein can be characterized by the following formula

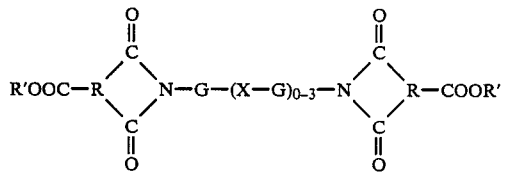

wherein each R is independently a trivalent organic radical, preferably a $C_2$ to $C_{20}$ aliphatic aromatic or cycloaliphatic trivalent organic radical; each R' is independently hydrogen or a monovalent aliphatic or cycloaliphatic radical containing 1–6 carbon atoms, or an aromatic radical containing 6–12 carbon atoms, e.g., benzyl, most preferably R' is hydrogen; and G is the radical remaining after the removal of the terminal (or as nearly terminal as possible) hydroxy groups of a long chain alkylene ether glycol having an average molecular weight of from about 600 to about 6000, and X is as follows:

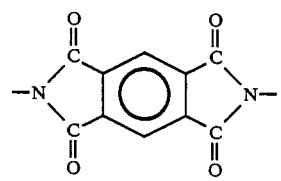

Representative long chain ether glycols from which the poly(oxyalkylene) diamine is prepared include poly(ethylene ether) glycol alone or in combination with other long chain ether glycols provided that the long chain glycols are selected so that the resulting poly(etherimide) ester elastomer contains about 25 weight percent to about 60 weight percent units of ethylene oxide. Representative long chain ether glycols that can be used with poly(ethylene oxide) glycols include poly(propylene ether) glycol; poly(tetramethylene ether) glycol; random or block copolymers of ethylene oxide and propylene oxide. Poly(ethylene oxide) glycol used alone is especially preferred.

In general, the poly(oxyalkylene) diamines have an average molecular weight of from about 600 to 6000, preferably from about 900 to about 4000.

The tricarboxylic component is a carboxylic acid anhydride containing an additional carboxylic group or the corresponding acid thereof containing two imide-forming vicinal carboxyl groups in lieu of the anhydride group. Mixtures thereof are also suitable. The additional carboxylic group must be esterifable and preferably, is substantially nonimidizable.

Further, while trimellitic anhydride is preferred as the tricarboxylic component, any of a number of suitable tricarboxylic acid constituents can be used including 2,6,7-naphthalenetricarboxylic anhydride; 3,3,,4-diphenyltricarboxylic anhydride; 3,3,,4-benzophenonetricarboxylic anhydride; 1,3,4-cyclopentanetricarboxylic anhydride; 2,2,,3-diphenyltricarboxylic anhydride; diphenyl sulfone-3,3,4-tricarboxylic anhydride; 3,4-dicarboxyphenyl-3,-carboxylphenyl ether anhydride;1,3,4-cyclohexanetricarboxylic anhydride; etc. These tricarboxylic acid materials can be characterized by the following formula:

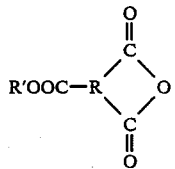

where R is a trivalent organic radical, preferably a $C_2$ to $C_{20}$ aliphatic, aromatic, or cycloaliphatic trivalent organic radical and R, is preferably hydrogen or a monovalent organic radical preferably a $C_1$ to $C_6$ aliphatic and/or cycloaliphatic radicals and $C_6$ to $C_{12}$ aromatic radicals, e.g. benzyl; most preferably hydrogen. As mentioned above, a portion of the tricarboxylic acid component can be replaced by pyromellitic anhydride.

Briefly, the poly(oxyalkylene imide) diacids may be prepared by known imidization reactions including melt synthesis or by synthesizing in a solvent system. Such reactions will generally occur at temperatures of from 100° C. to 300° C., preferably at from about 150° C. to about 250° C. while drawing off water or in a solvent system at the reflux temperature of the solvent or azeotropic (solvent) mixture.

For preparation of the poly(etherimide) ester elastomers, it is preferred that the diol be present in at least a molar equivalent amount, preferably a molar excess, most preferably 150 mole % based on the moles of dicarboxylic acid (b) and poly(oxyalkylene imide) diacid (c) combined. Such molar excess of diol will have a beneficial effect on the polymerization kinetics and ensure complete reaction of the acid components.

The weight ratios of poly(oxyalkylene imide) diacid (c) to dicarboxylic acid (b) is a necessary condition to maintain to form the poly(etherimide) ester elastomers. Compositions used in this invention are those in which the weight ratio of the poly(oxyalkylene imide) diacid (c) to dicarboxylic acid (b) is from about 0.5 to about 4.0, preferably from about 0.8 to about 3.0. The poly(etherimide) esters elastomers usually comprise the reaction product of dimethyl terephthalate, optionally with up to 40 mole % of another dicarboxylic acid; 1,4-butanediol, optionally with up to 40 mole % of another saturated or unsaturated aliphatic and/or cycloaliphatic diol; and a poly(oxyethylene imide) diacid prepared from a polyoxyalkylene diamine of molecular weight of from about 600 to about 6000, preferably from about 900 to about 4000, and trimellitic acid, optionally in the presence of pyromellitic anhydride.

The poly(etherimide ester) elastomers and process for their preparation are well known and more fully described in U.S. Pat. Nos. 4,556,705 and 4,556,688, the disclosures of which are incorporated herein by reference.

It is customery and preferred to utilize a catalyst in the process for the production of the poly(etherimide) ester elastomers. In general, any of the known ester-interchange and polycondensation catalysts may be used. Where the reactants and reactions allow, it is preferred to use the titanium catalysts including the inorganic and organic titanium containing catalysts.

The poly(etherimide) ester elastomers used to make the vapor permeable, waterproof film must contain at least about 25 weight percent repeating units of ethylene oxide and usually not more than about 60 percent by weight ethylene oxide units. Preferably, for a balance of desirable physical properties and desired water vapor transmission rate, the poly(etherimide) esters contain 30–55 weight percent repeating units of ethylene oxide. The presence of repeating units of ethylene oxide causes the polymer to be permeable to water vapor. The higher the percentage of repeating units of ethylene oxide in the polymer, the higher the degree of water vapor permeability.

The poly(etherimide) ester elastomer film can vary in thickness. However, usually the film is from about 0.3–6 mil thick, depending on the use contemplated. For use in tents the film is usually not greater than about 6 mil and when it is used in raincoats and jackets it is usually at least about 0.3 mil thick. The water vapor transmission rate for the hydrophilic film is at least about 3500 gm.mil/m²/24 hours according to ASTM E96-66 (Procedure BW), preferably 3500–20,000 gm.mil/m²/24 hours.

Although the poly(etherimide) ester elastomers possess many desirable properties, it is preferred to stabilize the compositions against heat, oxidation, radiation by UV light and the like. This can be accomplished by incorporating stabilizers in the compositions either during production or while in a hot melt stage following polymerization. The particular stabilizers useful in the present invention are any of those known in the art which are suitable for use with poly(etherimide) ester elastomers.

Various conventional fillers can be added to the poly(etherimide) ester elastomer to improve its physical properties, such as clay, talc, alumina, silica. The textile materials that are attached to the hydrophilic film can be coated with, for example, fluorocarbons or silicones, to render the article more water repellant.

The hydrophilic film is prepared as follows. The poly(etherimide) ester elastomer and additives, if any, are fed to an extruder and the polymer is heated above about its melting point. The film coming out of the extruder is melt coated on a support substrate, such as release paper, and wound and stored for use. The hydrophilic film can be used as surgical drape. Alternatively, the hydrophilic film can be made into a raincoat, jacket, tent, etc. by attaching it to a textile material, woven or nonwoven, such as poly(ethylene terephthalate), by sewing or by the spot application of a suitable adhesive on the textile material, such as a polyurethane adhesive.

The following examples are illustrative of the invention in which parts and percentages are by weight unless otherwise indicated.

INGREDIENTS USED

Poly(etherimide) ester elastomer A contained 53.8 weight percent 1,4-butylene terephthalate and 46.2 weight percent 1,4-butylene poly(oxyalkylene diimide) diacid ester. The diimide diacid was prepared by the imidization of trimellitic anhydride with Texaco Chemical Company's Jeffamine ED-2001, a predominately ethylene oxide containing copoly(ethylene oxide-propylene oxide) diamine, number average molecular weight 2000. The poly(etherimide) ester had a calculated amount of 34.2 weight percent ethylene oxide units.

Poly(etherimide) ester elastomer B contained 40 weight percent 1,4-butylene terephthalate and 60 weight percent 1,4-butylene poly(oxyalkylene diimide) diacid ester. The diimide diacid was prepared by the imidization of trimellitic anhydride with above-described Texaco Chemical Company's Jeffamine ED-2001. The poly(etherimide) ester had a calculated amount of 44.4 weight percent ethylene oxide units.

Poly(etherimide) ester elastomer C contained 34 weight percent 1,4-butylene terephthalate, 6 weight percent 1,4-butylene isophthalate and 60 weight percent poly(oxyalkylene diimide) diacid ester. The diimide diacid was prepared by the imidization of trimellitic anhydride with above-described Texaco Chemical Company's Jeffamine ED-2001. The poly(etherimide) ester had a calculated amount of 44.4 weight percent ethylene oxide units.

Poly(etherimide) ester elastomer D contained 54.0 weight percent 1,4-butylene terephthalate and 46 weight percent 1,4-butylene poly(oxyalkylene tetraimide) diacid ester. The tetraimide diacid was prepared by reacting first 2 moles of Jeffamine ED 2001 with one mole of pyromelletic dianhydride followed by imidization of the remaining amino groups with trimellitic anhydride. The poly(etherimide) ester had a calculated amount of 35.6 weight percent ethylene oxide units. Optionally, the tetraimide diacid can be prepared directly by using a mixture of pyromellitic dianhydride and trimellitic anhydride in the molar ratio of 0.5/1.0.

EXAMPLES 1-4

The poly(etherimide) ester elastomers listed in Table 1 below were extruded into a film on an extrusion line which consisted of a 28 mm diameter Werner Pfleiderer twin screw extruder, a 10 inch wide die having a 0.010 inch gap, a quench roll and wind-up roll. The extruder and die were heated to 210° C. which is about 10° to 15° C. above the polymer melting point. The polymer was extruded through the die using a screw speed of 100 rpm. The molten polymer film exiting the die was drawn down to the final film thickness as indicated below, by controlling the quench drum speed. The quench drum temperature was maintained at 60° C.

TABLE 1

| Example | Elastomer | EO, % | Thickness, mils | WVTR* |
|---|---|---|---|---|
| 1 | A | 34.2 | 0.7 | 13700 |
| 2 | B | 44.4 | 1.0 | 18900 |
| 3 | C | 44.4 | 1.4 | 20000 |
| 4 | D | 35.6 | 1.2 | 29400 |

*gms · m²/24 hrs. (ASTM E96-66BW)

EXAMPLES 5-6

Films of examples 2 and 3 described above were heat laminated to a powder bonded non-woven fabric of poly(ethylene terephthalate) at 160° C. The WVTR of the film-fabric laminates were 13,200 and 13,800 gm.m2/24 hrs, respectively.

We claim:
1. A flexible breathable waterproof product which comprises a film of a thermoplastic hydrophilic poly(etherimide) ester elastomer 0.3-6 mil thick comprising the reaction product of one or more diols, one or more dicarboxylic acids, and one or more poly(oxyalkylene imide) diacids said poly(oxyalkylene imide) diacid containing sufficient repeating units of ethylene oxide so that the resulting poly(etherimide) ester elastomer contains about 25-60 weight percent ethylene oxide units said film has a water vapor transmission rate of at least about 3500 gm.mil/m²/24 hrs. according to ASTM E96-66 (Procedure BW).

2. A flexible breathable waterproof product which comprises a film of a thermoplastic hydrophilic poly(etherimide) ester elastomer comprising the reaction product of one or more diols, one or more dicarboxylic acids, and one or more poly(oxyalkylene imide) diacids having the formula

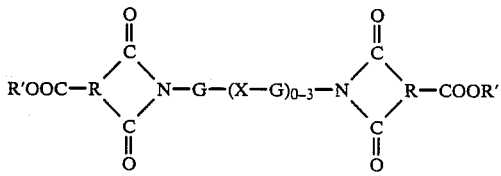

wherein each R is independently a trivalent organic radical, R' is independently hydrogen or a monovalent aliphatic or cycloaliphatic radical containing 1 to 6 carbon atoms or an aromatic radical containing 6-12 carbon atoms, G is radical remaining after the removal of the terminal hydroxy groups of a long chain alkylene ether glycol having an average molecular weight of from about 600-6000, and X has the formula

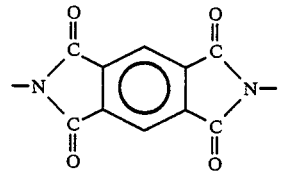

said poly(oxyalkylene imide) diacid contains sufficient repeating units of ethylene oxide so that the resulting poly(etherimide) ester elastomer contains about 25-60 weight percent ethylene oxide units and said film has a water vapor transmission rate of at least about 3500 gm.mil/m²/24 hrs. according to ASTM E96-66 (Procedure BW).

3. A flexible breathable product for use in waterproof articles which comprises a textile material attached to a film of a thermoplastic hydrophilic poly(etherimide) ester elastomer of claim 1.

4. A flexible breathable product for use in waterproof articles which comprises a textile material attached to a film of a thermoplastic hydrophilic poly(etherimide) ester elastomer of claim 2.

5. A flexible breathable product of claim 2 wherein the poly(oxyalkylene imide) diacid is derived from a polyoxyalkylene diamine and trimellitic anhydride.

6. A flexible breathable product of claim 2 wherein the poly(oxyalkylene imide) diacid is derived from a polyoxyalkylene diamine and a mixture of trimellitic anhydride and pyromellitic anhydride.

7. A flexible breathable product of claim 2 wherein the poly(oxyalkylene imide) diacid is poly(oxyethylene imide) diacid.

8. A flexible breathable product of claim 2 wherein the diol is 1,4-butanediol, the dicarboxylic acid is terephthalic acid or mixtures of terephthalic acid with phthalic acid or isophthalic acid and the poly(oxyalkylene imide) diacid is poly(oxyethylene imide) diacid.

9. A flexible layered product of claim 3 wherein the textile material is poly(ethylene terephthalate).

* * * * *